US010267755B2

(12) United States Patent
Kishi et al.

(10) Patent No.: US 10,267,755 B2
(45) Date of Patent: Apr. 23, 2019

(54) METHOD FOR INSPECTING CRYSTAL UNIT BY ANALYZING FREQUENCY CHARACTERISTICS OF IMPEDANCE

(71) Applicant: FUJITSU LIMITED, Kawasaki-shi, Kanagawa (JP)

(72) Inventors: Masakazu Kishi, Kawasaki (JP); Hajime Kubota, Kawasaki (JP); Masayuki Itoh, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 182 days.

(21) Appl. No.: 14/970,651

(22) Filed: Dec. 16, 2015

(65) Prior Publication Data
US 2016/0223391 A1 Aug. 4, 2016

(30) Foreign Application Priority Data
Feb. 2, 2015 (JP) ................. 2015-018791

(51) Int. Cl.
*H03B 5/32* (2006.01)
*H03B 5/36* (2006.01)
(Continued)

(52) U.S. Cl.
CPC ............ *G01N 27/02* (2013.01); *G01H 15/00* (2013.01); *G01N 27/028* (2013.01); *G01R 23/02* (2013.01); *G01R 27/16* (2013.01); *G01R 29/22* (2013.01); *G01R 31/2824* (2013.01); *H03B 5/323* (2013.01); *H03B 5/36* (2013.01); *H03H 9/1021* (2013.01)

(58) Field of Classification Search
CPC .... G01R 29/22; G01R 27/00; G01R 31/2824; G01R 23/02; G01H 15/00; H03B 4/323; G01N 27/02; G01N 27/028

USPC ................ 324/76.49, 727, 619; 331/44, 163, 331/158–162, 164; 73/588, 582, DIG. 4, 73/576, 574; 29/25.35, 593
See application file for complete search history.

(56) References Cited

U.S. PATENT DOCUMENTS 2,440,886 A * 5/1948 Bach ...................... G01R 29/22
310/311
2,476,954 A * 7/1949 Blackburn ............. G01R 29/22
324/119
(Continued)

FOREIGN PATENT DOCUMENTS

JP 2004-007469 1/2004
JP 2011-135342 7/2011

OTHER PUBLICATIONS

Cartright et al, Aging Performance in Crystals, Oct. 2008, Connor Winfield.*
(Continued)

*Primary Examiner* — Daniel S Larkin
*Assistant Examiner* — David L Singer
(74) *Attorney, Agent, or Firm* — Fujitsu Patent Center (57) ABSTRACT

A method for inspecting a crystal unit, the method includes: generating a sub-vibration in a crystal blank of the crystal unit by applying an input signal to a plurality of electrodes formed on the crystal blank; obtaining frequency characteristics of impedance between the plurality of electrodes from an output signal of the plurality of electrodes; and comparing the frequency characteristics obtained with reference frequency characteristics indicating quality of the crystal unit.

6 Claims, 11 Drawing Sheets

(51) Int. Cl.
*H03H 9/10* (2006.01)
*G01H 15/00* (2006.01)
*G01N 27/02* (2006.01)
*G01R 23/02* (2006.01)
*G01R 27/16* (2006.01)
*G01R 29/22* (2006.01)
*G01R 31/28* (2006.01)

(56) References Cited

U.S. PATENT DOCUMENTS

| | | | | |
|---|---|---|---|---|
| 2,846,874 | A * | 8/1958 | Horn | G01N 29/04 |
| | | | | 310/317 |
| 4,387,503 | A * | 6/1983 | Aswell | H01L 21/268 |
| | | | | 148/DIG. 91 |
| 5,319,324 | A | 6/1994 | Satoh | |
| 6,696,898 | B1 * | 2/2004 | Ward | H01F 17/0006 |
| | | | | 257/E27.046 |
| 7,424,827 | B2 * | 9/2008 | Yamada | G01N 29/045 |
| | | | | 73/579 |
| 8,304,961 | B2 * | 11/2012 | Goto | G01N 29/12 |
| | | | | 310/318 |
| 2006/0139115 | A1 | 6/2006 | Mizumura | |
| 2007/0040470 | A1 | 2/2007 | Watanabe | |
| 2007/0075796 | A1 * | 4/2007 | Mizumura | H03B 5/04 |
| | | | | 331/158 |
| 2007/0120614 | A1 * | 5/2007 | Moriya | H03H 9/0547 |
| | | | | 331/158 |
| 2007/0229178 | A1 * | 10/2007 | Harima | H03B 5/32 |
| | | | | 331/158 |
| 2009/0066190 | A1 | 3/2009 | Harima | |
| 2009/0066426 | A1 * | 3/2009 | Harima | H03H 9/0547 |
| | | | | 331/44 |
| 2009/0160561 | A1 * | 6/2009 | Murase | H03H 9/0547 |
| | | | | 331/44 |
| 2009/0167448 | A1 * | 7/2009 | Yamakawa | H03B 5/32 |
| | | | | 331/68 |
| 2011/0156823 | A1 | 6/2011 | Koyama et al. | |
| 2012/0056684 | A1 | 3/2012 | Kishi | |
| 2012/0062072 | A1 | 3/2012 | Kubota et al. | |
| 2012/0112761 | A1 * | 5/2012 | Sonnhueter | G01R 31/2824 |
| | | | | 324/537 |
| 2013/0213137 | A1 * | 8/2013 | Ostapenko | G01N 29/12 |
| | | | | 73/582 |
| 2015/0116044 | A1 * | 4/2015 | Itasaka | H03B 5/362 |
| | | | | 331/62 |
| 2016/0223391 | A1 | 8/2016 | Kishi et al. | |

OTHER PUBLICATIONS

MtronPTI, Understanding Quartz Crystals, Aug. 25, 2014.*
Vectron International, Aging and Retrace in Oven Controlled Crystal Oscillators, Aug. 16, 2011.*
Matthys, Crystal Oscillator Circuits, 1992, Krieger Publishing Company, Revised Edition.*
U.S. Office Action dated Dec. 5, 2017 for co-pending U.S. Appl. No. 14/974,434, 9 pages.
U.S. Office Action dated Nov. 1, 2017 for co-pending U.S. Appl. No. 14/974,434, 6 pages.
U.S. Office Action dated Jan. 31, 2018 for co-pending U.S. Appl. No. 14/974,434, 5 pages.
U.S. Office Action dated Mar. 26, 2018 for co-pending U.S. Appl. No. 15/890,468, 12 pages.

* cited by examiner

METHOD FOR INSPECTING CRYSTAL UNIT BY ANALYZING FREQUENCY CHARACTERISTICS OF IMPEDANCE

CROSS-REFERENCE TO RELATED APPLICATION

This application is based upon and claims the benefit of priority of the prior Japanese Patent Application No. 2015-018791, filed on Feb. 2, 2015, the entire contents of which are incorporated herein by reference.

FIELD

The embodiments discussed herein are related to a method for inspecting a crystal unit.

BACKGROUND

There has been known a piezoelectric oscillator which includes an auxiliary oscillator having an auxiliary electrode formed separately from a main electrode on a piezoelectric substrate, detects a frequency of an oscillation output signal of the auxiliary oscillator, and estimates a temperature of a crystal unit based on the frequency and the temperature characteristics of the frequency of the auxiliary oscillator.

In recent years, in an effort to meet the requirements of reduction in device size, compactness and high-density packaging of parts and modules are in progress. With no exception, the downsizing of the crystal units serving as clock sources have also been in progress. Under such circumstances, when it is considered that a function failure has occurred in a device due to abnormality of a crystal unit, it is useful to provide the ability to inspect the electrical characteristics of the crystal unit in a state where it is packaged into the device. This is because it is difficult to take out and inspect only the crystal unit for the reason that peripheral parts may be damaged when the crystal unit is removed from the device in a high-density packaging state.

The following is a reference document.

[Document 1] Japanese Laid-Open Patent Publication No. 2011-135342.

SUMMARY

According to an aspect of the invention, a method for inspecting a crystal unit, the method includes: generating a sub-vibration in a crystal blank of the crystal unit by applying an input signal to a plurality of electrodes formed on the crystal blank; obtaining frequency characteristics of impedance between the plurality of electrodes from an output signal of the plurality of electrodes; and comparing the frequency characteristics obtained with reference frequency characteristics indicating quality of the crystal unit.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

Hereinafter, various embodiments will now be described in detail with reference to the accompanying drawings.

A method of inspecting a crystal unit according to one embodiment will be described with reference to FIGS. 1 to 10.

Figure 1A:
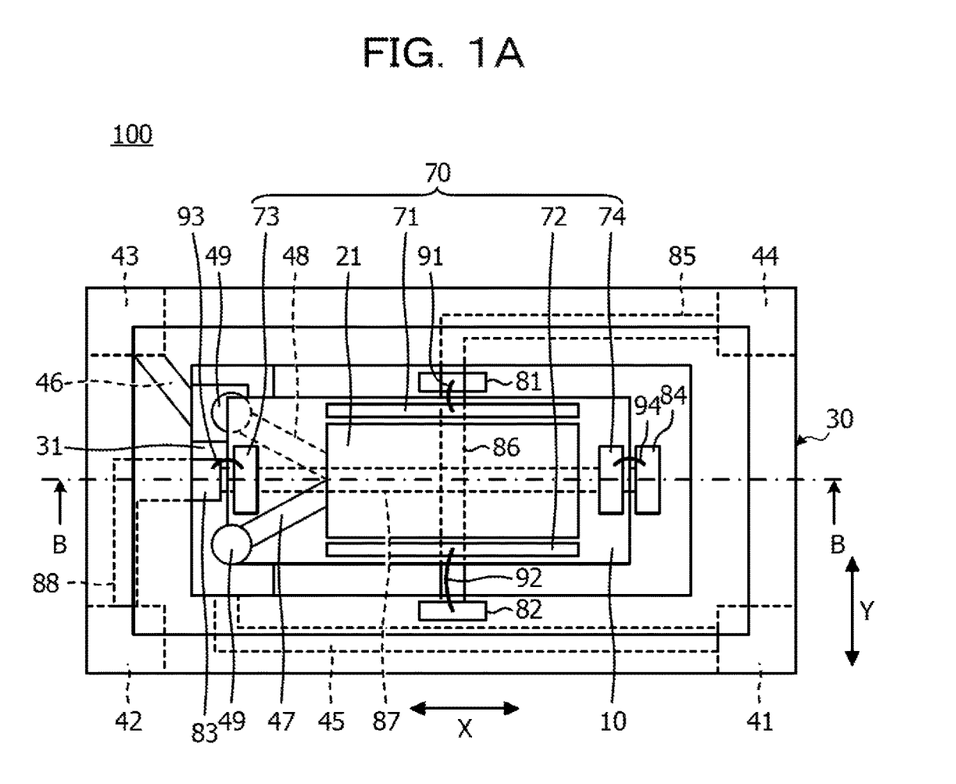
FIGS. 1A and 1B each is a view schematically illustrating a crystal unit 100 according to one example.
Figure 1B:
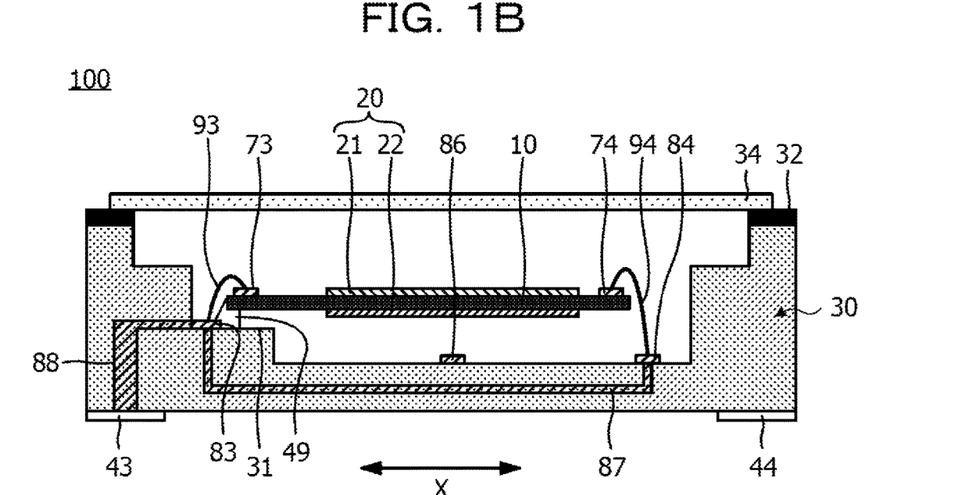

FIGS. 1A and 1B each is a view schematically illustrating a crystal unit 100 according to one example to which the inspecting method according to one embodiment may be suitably applied, FIG. 1A being a top view and FIG. 1B being a sectional view taken along line B-B in FIG. 1A. In FIG. 1A, a cover of a housing 30 is not illustrated to allow the interior of the housing 30 to be visible. In the following description, with the thickness direction of a crystal blank 10 (e.g., the vertical direction of FIGS. 1A and 1B) assumed as a vertical direction, a side in which the cover of the housing 30 is placed is referred to as an "upper side." However, the orientation of the mounting state of the crystal unit 100 is optional. An X direction is defined by a direction corresponding to the main vibration direction of the crystal unit 100, as illustrated in FIG. 1A, and a Y direction is defined by a direction which is parallel to the surface of the crystal blank 10 and perpendicular to the main vibration direction of the crystal unit 100, as illustrated in FIG. 1A.

The crystal unit 100 includes the crystal blank 10, an excitation electrode 20, the housing 30, external electrodes 41 to 44 and a sub-vibration electrode 70. The crystal unit 100 is of a surface mounting type, as illustrated in FIGS. 1A and 1B.

The crystal blank 10 may be, for example, an AT-cut artificial crystal substrate. The crystal blank 10 may be supported in a cantilever structure to the housing 30. In the example illustrated in FIGS. 1A and 1B, the crystal blank 10 is supported in a cantilever structure on a dam portion 31 of the housing 30. In the example illustrated in FIGS. 1A and 1B, in an operation of the crystal unit 100, the crystal blank 10 is intended to vibrate in the X direction (e.g., a thickness sliding vibration). In addition, the crystal blank 10 may be cantilevered at the end of the Y direction. Hereinafter, the vibration of the crystal blank 10 in the X direction (e.g., a thickness sliding vibration) is called a "main vibration."

In an operation of the crystal unit 100, the excitation electrode 20 excites the main vibration of the crystal blank 10. The excitation electrode 20 includes an upper excitation electrode 21 formed on the upper surface of the crystal blank 10 and a lower excitation electrode 22 formed on the lower surface of the crystal blank 10. In an operation of the crystal unit 100, the main vibration of the crystal blank 10 is excited by a potential difference between the upper excitation electrode 21 and the lower excitation electrode 22.

The housing 30 accommodates the crystal blank 10. The housing 30 is a ceramic package formed of, for example, a ceramic material. The housing 30 includes a cover 34 and encapsulates the crystal blank 10 in the inner space of the housing 30 in an airtight manner. For example, the inner space of the housing 30 is in a vacuum state or is filled with dry nitrogen and is sealed by the cover 34. In the example illustrated in FIGS. 1A and 1B, the cover 34 is coupled to the body of the housing 30 via a seal member 32.

The external electrodes 41 to 44 are disposed in the housing 30. In the example illustrated in FIGS. 1A and 1B, the external electrodes 41 to 44 are disposed on the outer surface of the bottom of the housing 30. The external electrodes 41 and 43 are electrically connected to the upper excitation electrode 21 and the lower excitation electrode 22, respectively. In the example illustrated in FIGS. 1A and 1B, the external electrode 41 is electrically connected to the upper excitation electrode 21 via a conductor pattern 45 formed on the inner layer of the housing 30 and a conductor pattern 47 formed on the top surface of the crystal blank 10.

The conductor pattern 45 is exposed from the inner layer of the housing 30 to the front surface thereof at both ends; one end being electrically connected to the external electrode 41 and the other end being electrically connected to the conductor pattern 47 by a conductive adhesive 49. Similarly, the external electrode 43 is electrically connected to the lower excitation electrode 22 via a conductor pattern 46 formed on the inner layer of the housing 30 and a conductor pattern 48 formed on the bottom surface of the crystal blank 10. The conductor pattern 46 is exposed from the inner layer of the housing 30 to the front surface thereof at both ends; one end being electrically connected to the external electrode 43 and the other end being electrically connected to the conductor pattern 48 by the conductive adhesive 49. The conductive adhesive 49 is formed on the edge of the crystal blank 10 (e.g., the edge of the cantilevered side).

The sub-vibration electrode 70 includes first to fourth sub-electrodes 71 to 74. The first to fourth sub-electrodes 71 to 74 are disposed on the surface of the crystal blank 10. The first to fourth sub-electrodes 71 to 74 are disposed around the upper excitation electrode 21 at a distance from the upper excitation electrode 21.

In the example illustrated in FIGS. 1A and 1B, the first to fourth sub-electrodes 71 to 74 are formed as follows. The first to fourth sub-electrodes 71 to 74 are disposed on the upper surface of the crystal blank 10. The first and second sub-electrodes 71 and 72 are disposed with the upper excitation electrode 21 interposed therebetween in the Y direction. The third and fourth sub-electrodes 73 and 74 are disposed with the upper excitation electrode 21 interposed therebetween in the X direction. The first sub-electrode 71 is electrically connected to a first housing side electrode 81, which is formed on the dam portion 31, via a wire 91 by means of bonding. Similarly, the second to fourth sub-electrodes 72 to 74 are electrically connected to second to fourth housing side electrode 82 to 84, which are formed on the inner surface of the bottom of the housing 30 (e.g., the surface of the inside of the housing 30), via wires 92 to 94, respectively.

The first housing side electrode 81 is electrically connected to an external electrode 44 via a conductor pattern 85 formed on the inner layer of the housing 30. The second housing side electrode 82 is electrically connected to the first housing side electrode 81 via a conductor pattern 86 formed on the inner surface of the bottom of the housing 30. As a result, the second housing side electrode 82 is electrically connected to the external electrode 44 via the conductor pattern 86, the first housing side electrode 81, and the conductor pattern 85.

In addition, the third housing side electrode 83 is electrically connected to an external electrode 42 via a conductor pattern 88 formed on the inner layer of the housing 30. The fourth housing side electrode 84 is electrically connected to the third housing side electrode 83 via a conductor pattern 87 formed on the inner layer of the housing 30. As a result, the fourth housing side electrode 84 is electrically connected to the external electrode 42 via the conductor pattern 87, the third housing side electrode 83, and the conductor pattern 88.

Figure 2:
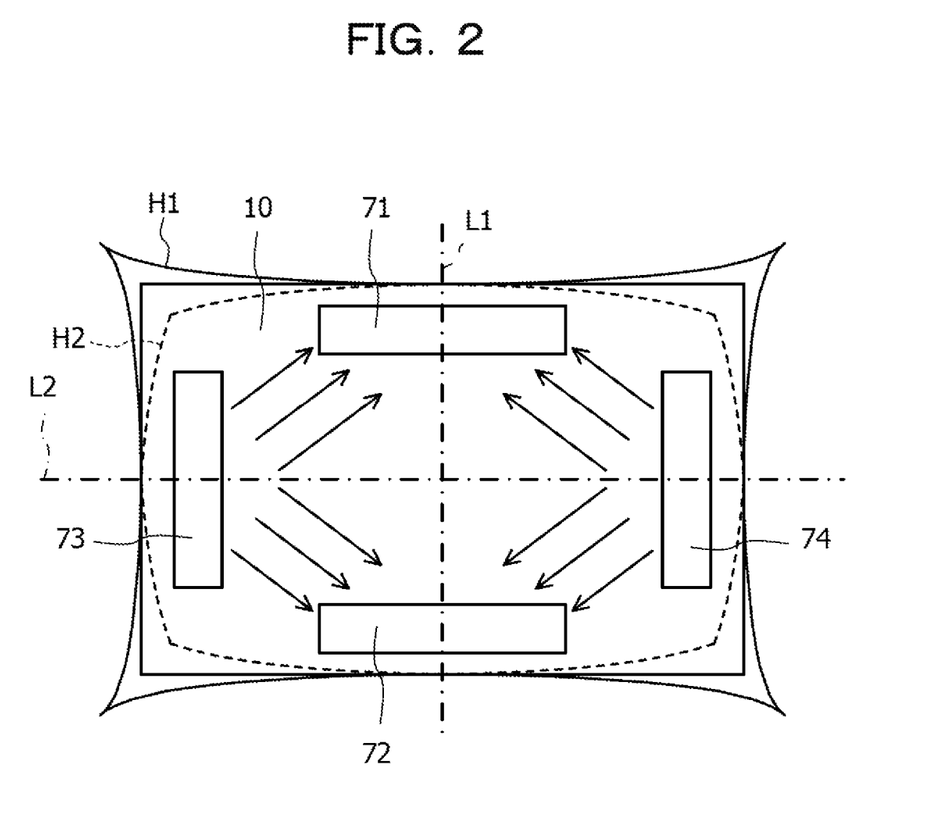
FIG. 2 is an explanatory view of sub-vibration excited by a sub-vibration electrode 70.

FIG. 2 is an explanatory view of the sub-vibration excited by the sub-vibration electrode 70, schematically illustrating only the crystal blank 10 and the sub-vibration electrode 70 when viewed from the top. In FIG. 2, reference numerals H1 and H2 schematically represent a change in shape (e.g., contour) of the crystal blank 10 due to a displacement by the sub-vibration. In FIG. 2, the arrows among the first to fourth sub-electrodes 71 to 74 represent the direction of an electric field produced among the first to fourth sub-electrodes 71 to 74 at certain timing in the inspection of the crystal unit 100.

The sub-vibration electrode 70 excites the sub-vibration of the crystal unit 100 in the inspection of the crystal unit 100. Specifically, a first signal of a sinusoidal wave is applied to the first sub-electrode 71 and the second sub-electrode 72 and a second signal of a sinusoidal wave having the opposite phase to the first signal is applied to the third sub-electrode 73 and the fourth sub-electrode 74. As a result, an alternating electric field is produced between the first sub-electrode 71 and the third sub-electrode 73, between the first sub-electrode 71 and the fourth sub-electrode 74, between the second sub-electrode 72 and the third sub-electrode 73 and between the second sub-electrode 72 and the fourth sub-electrode 74.

The arrows of the electric field illustrated in FIG. 2 represent the direction of the electric field under a state where a negative voltage is applied to the first sub-electrode 71 and the second sub-electrode 72 (therewith, under a state where a positive voltage is applied to the third sub-electrode 73 and the fourth sub-electrode 74). At this time, the crystal blank 10 is displaced in a manner illustrated in the outline H1. When an electric field is produced in the opposite direction to the electric field direction illustrated in FIG. 2, the crystal blank 10 is displaced in a manner illustrated in the outline H2. In this manner, it is possible to excite the sub-vibration of the crystal unit 100 by producing the alternating electric field among the first to fourth sub-electrodes 71 to 74. The sub-vibration of the form as illustrated in FIG. 2 involves a change in contour of the crystal blank 10 and is called a contour vibration. The support point of the crystal blank 10 (e.g., the position of the conductive adhesive 49) is preferably set on or near the nodal lines L1 and L2 of the contour vibration in order to minimize an effect of the support point on the contour vibration.

Figure 3:
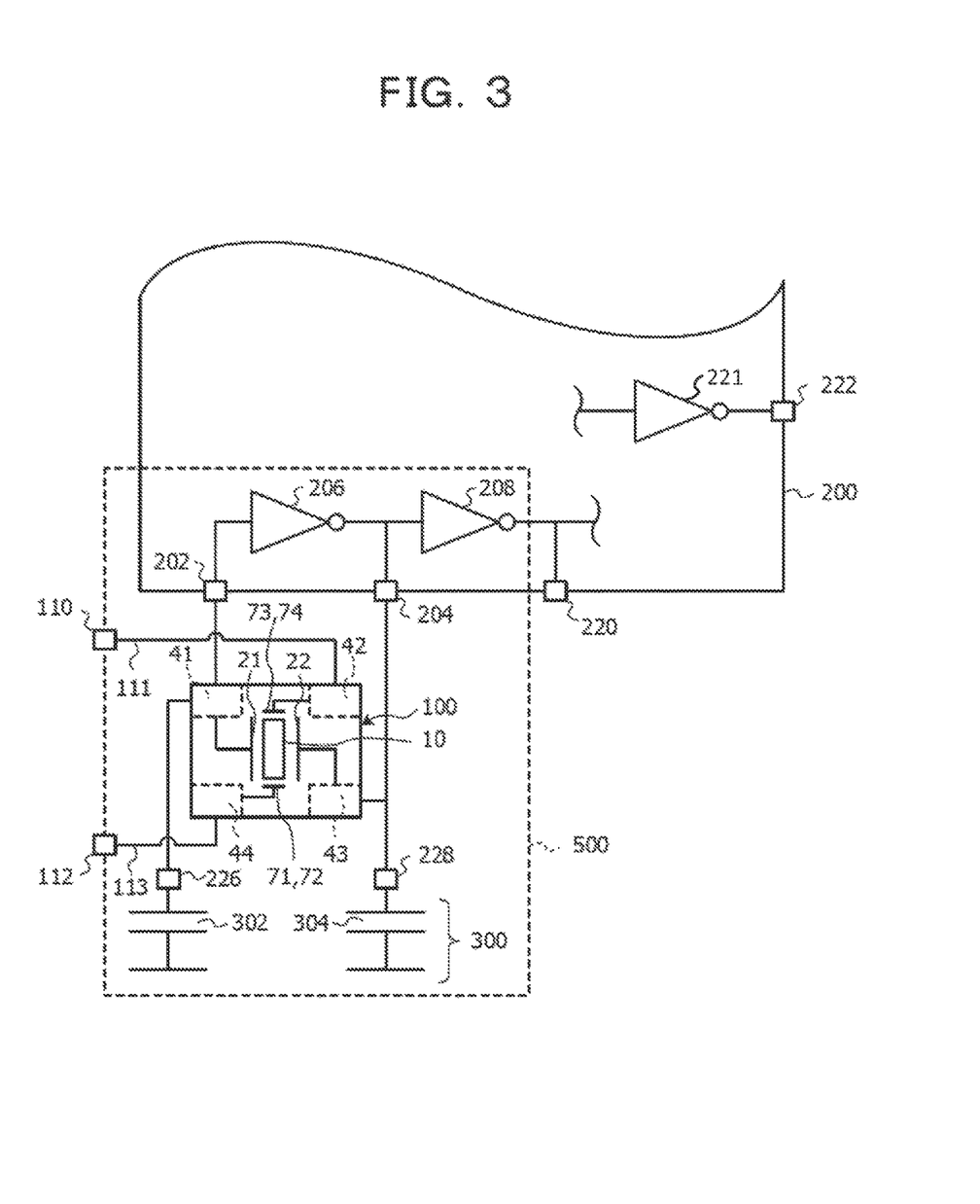
FIG. 3 is a view schematically illustrating one example of the circuit configuration incorporating the crystal unit 100.

FIG. 3 is a view schematically illustrating one example of the circuit configuration incorporating the crystal unit 100.

In the example illustrated in FIG. 3, the crystal unit 100 is connected to an IC 200. Specifically, the external electrodes 41 and 43 of the crystal unit 100 are connected to terminals 202 and 204 of the IC 200, respectively. The crystal unit 100 generates clocks to be used in the IC 200. The IC 200 includes an inverting amplifier 206 and output buffers 208, 221. A signal input to the terminal 202 is inverted and amplified by the inverting amplifier 206. The inverted and amplified signal is input to the output buffer 208 and is supplied to the upper excitation electrode 21 via the external electrode 43. In the example illustrated in FIG. 3, the upper excitation electrode 21 and the lower excitation electrode 22 may be reversely arranged.

A matching capacitor 300 is connected to the crystal unit 100. Specifically, a first capacitor 302 is connected between the external electrode 41 of the crystal unit 100 and a ground and a second capacitor 304 is connected between the external electrode 43 of the crystal unit 100 and the ground. With respect to the IC 200, an internal capacitance of the terminals, a stray capacitance of wiring patterns of a mounting substrate, a resistor limiting a current flowing through the crystal unit 100, etc., are not illustrated in FIG. 3. The matching capacitor 300 is formed to adjust an oscillation frequency (e.g., matching adjustment) of the crystal unit 100 to a desired value (e.g., a designed value) when the total of capacitance (e.g., a load capacitance) including all circuit elements ranging from the crystal unit 100 to the IC 200 is assumed as a load. In FIG. 3, a range surrounded by a dotted line forms an oscillation circuit 500 pertaining to the main vibration (hereinafter, referred to as "main vibration oscillation circuit 500.")

Figure 4:
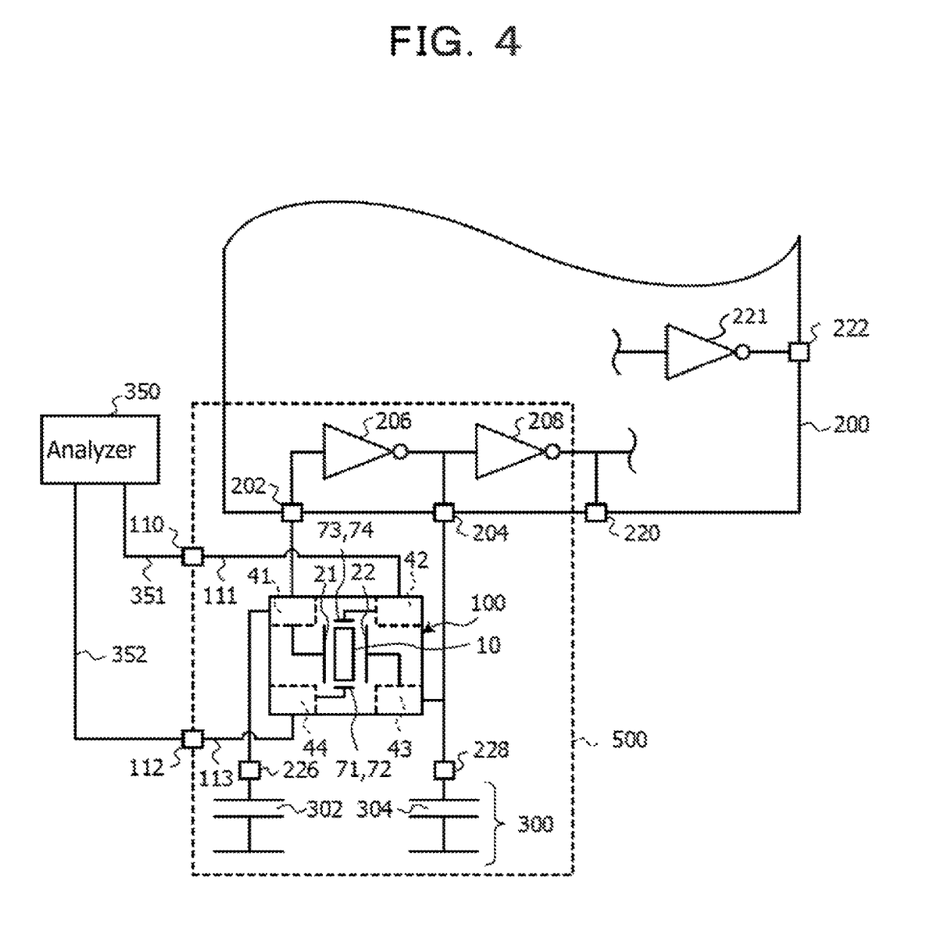
FIG. 4 is an explanatory view of a method of inspecting the crystal unit 100.

Wirings 111 and 113 are connected to the crystal unit 100. The wiring 111 has one end connected to the external electrode 42 and the other end connected to an external monitor terminal 110. The wiring 113 has one end connected to the external electrode 44 and the other end connected to an external monitor terminal 112. The wirings 111 and 113 and the external monitor terminals 110 and 112 may be formed on, for example, a board 900 (see, e.g., FIG. 10) on which the crystal unit 100 is mounted. As illustrated in FIG. 4, the wirings 111 and 113 and the external monitor terminals 110 and 112 are electrically isolated from the main vibration oscillation circuit 500. The wirings 111 and 113 and the external monitor terminals 110 and 112 are used to inspect the crystal unit 100 based on the sub-vibration, which will be described later.

The IC 200 may have terminals 220 and 222 for monitoring the main vibration oscillation circuit 500. However, these terminals 220 and 222 may be omitted. This is because the crystal unit 100 may be inspected based on the sub-vibration by forming the wirings 111 and 113 and the external monitor terminals 110 and 112 in this embodiment, as will be described later.

FIG. 4 is an explanatory view of a method of inspecting the crystal unit 100, schematically illustrating a state in the inspection.

The method of inspecting the crystal unit 100 to be described below may be performed under a state where the crystal unit 100 is mounted. Specifically, an analyzer 350 such as a network analyzer or a spectrum analyzer is connected to the mounted crystal unit 100, as schematically illustrated in FIG. 4. Wirings 351 and 352 are formed by applying, for example, a probe (not illustrated) to the external monitor terminals 110 and 112. To this end, the external monitor terminals 110 and 112 are set at a position where the probe may be easily applied to the terminals 110 and 112 under the state where the crystal unit 100 is mounted. If the probe may be directly and easily applied to the external electrodes 42 and 44 under the state where the crystal unit 100 is mounted, the wirings 111 and 113 and the external monitor terminals 110 and 112 may be omitted. In this case, an inspector may make an electrical connection of the analyzer 350 to the external electrodes 42 and 44 by directly applying the probe to the external electrodes 42 and 44 under the state where the crystal unit 100 is mounted.

The inspector applies an input signal from the analyzer 350 to the sub-vibration electrode 70 of the crystal unit 100 via the wirings 351 and 352 under a state where the main vibration of the crystal unit 100 is stopped. For example, as the input signal, the first signal of the sinusoidal wave is input via the wiring 351 and the second signal of the sinusoidal wave having the opposite phase to the first signal is input via the wiring 352. The state where the main vibration of the crystal unit 100 is stopped corresponds to a state where the inverting amplifier 206 is powered off. At this time, the inspector scans (changes) the frequency of the input signal from the analyzer 350 in order to excite the sub-vibration. As a result, the inspector obtains an output for the input signal applied to the crystal unit 100 (e.g., an output obtained via the wirings 351 and 352) via the analyzer 350. The analyzer 350 outputs the frequency characteristics of impedance between the external electrodes 42 and 44 based on the output (response) obtained via the wirings 351 and 352. Thus, by connecting the analyzer 350 to the external monitor terminals 110 and 112 and applying the input signal to the crystal unit 100, it is possible to obtain the frequency characteristics of impedance between the external electrodes 42 and 44 from the external monitor terminals 110 and 112.

Figure 5:
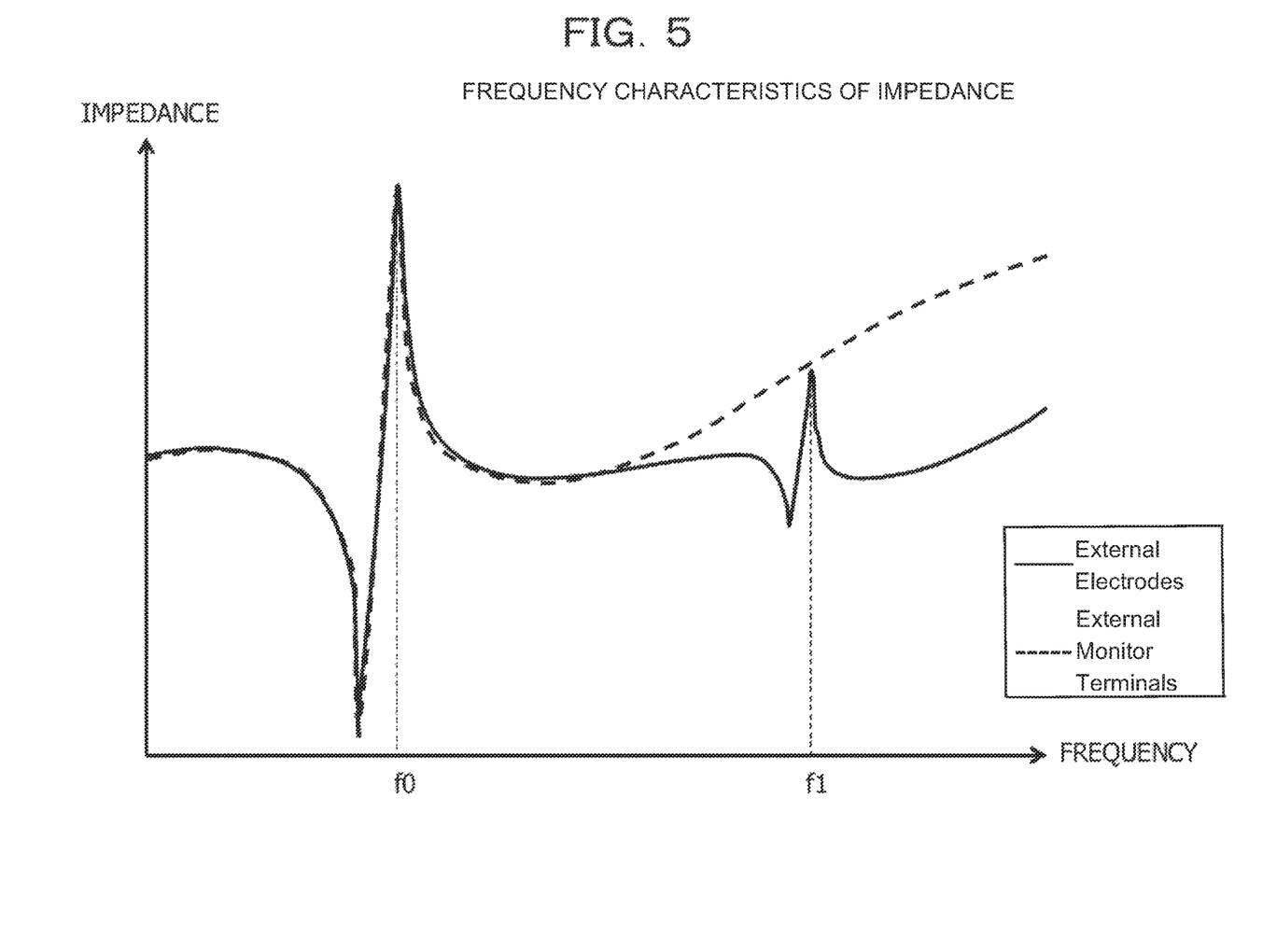
FIG. 5 is a view illustrating one example of the frequency characteristics of impedance between external electrodes 42 and 44 according to the sub-vibration.

FIG. 5 is a view illustrating one example of the frequency characteristics of impedance between the external electrodes 42 and 44 (e.g., characteristics according to the sub-vibration). In FIG. 5, as the frequency characteristics of impedance between the external electrodes 42 and 44, the frequency characteristics of impedance obtained from the external monitor terminals 110 and 112 are indicated by a broken line. In addition, in FIG. 5, as the frequency characteristics of impedance between the external electrodes 42 and 44, the characteristics in the single crystal unit 100 (hereinafter referred to as "single-unit characteristics") are together indicated by a solid line for reference. The single-unit characteristics of the crystal unit 100 are obtained by taking out the crystal unit 100 alone and observing it from between the external electrodes 42 and 44. The phrase "taking out the crystal unit 100 alone" as used herein means that the crystal unit 100 is not placed under a mounted state.

In the single-unit characteristics of the crystal unit 100, as illustrated in FIG. 5, the main vibration (e.g., frequency f1) has a smaller response than the sub-vibration (e.g., frequency f2). This is because the main vibration itself is stationary although some main vibration occurs derivatively due to the input signal from the analyzer 350 (i.e., because the inverting amplifier 206 illustrated in FIG. 4 is turned off). The characteristics illustrated in FIG. 5 are illustrative only and do not necessarily have the illustrated response ratio of the sub-vibration to the main vibration.

Figure 6:
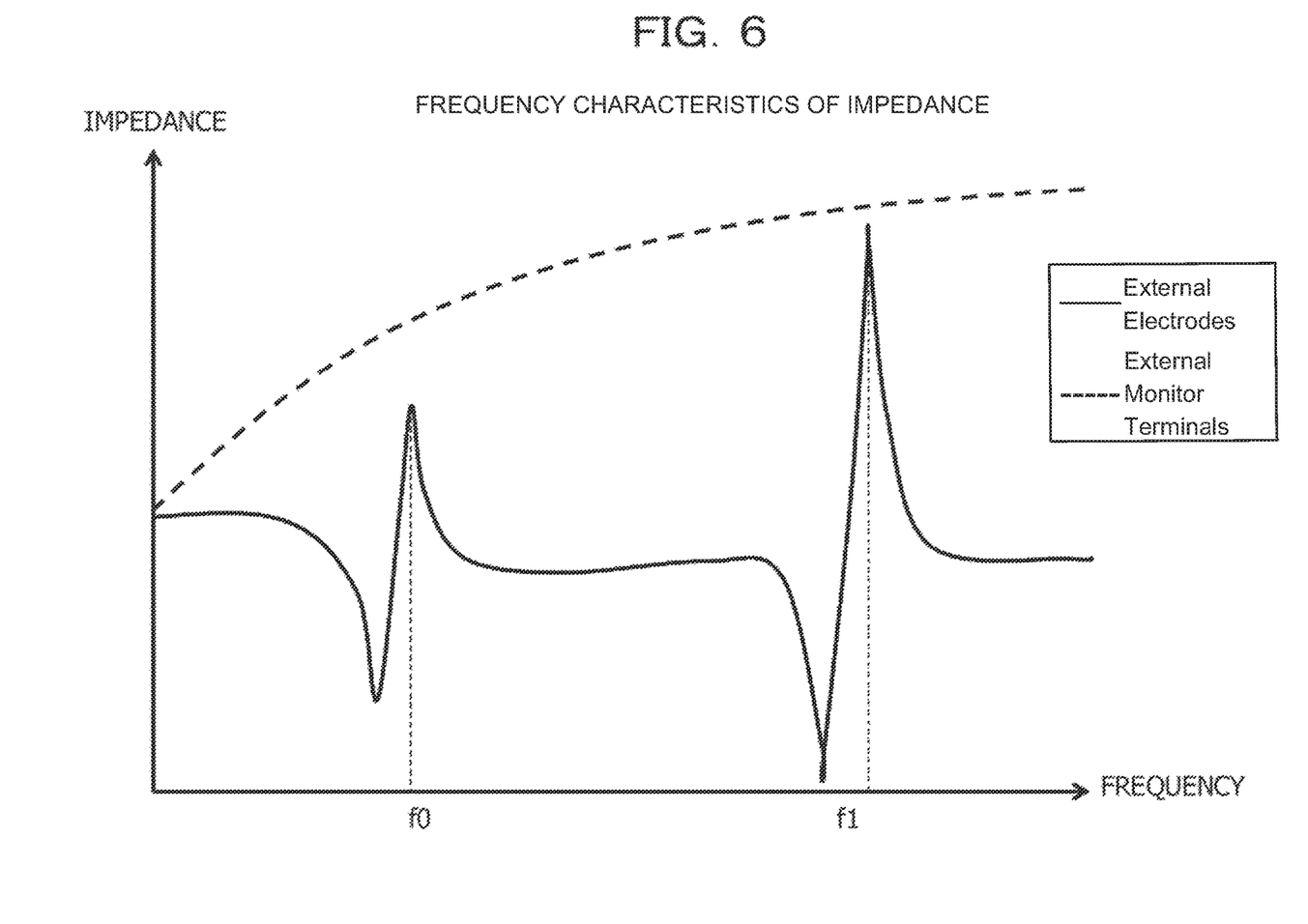
FIG. 6 is a view illustrating one example of the frequency characteristics of impedance between external electrodes 41 and 43 according to main vibration.

FIG. 6 is a view illustrating one example of the frequency characteristics of impedance between the external electrodes 41 and 43 (e.g., the characteristics according to the main vibration), for comparison. In FIG. 6, as the frequency characteristics of impedance between the external electrodes 41 and 43, the frequency characteristics of impedance obtained from the terminals 202 and 204 (or the terminals 226 and 228) are indicated by a broken line. In addition, in FIG. 6, as the frequency characteristics of impedance between the external electrodes 41 and 43, the single-unit characteristics of the crystal unit 100 are together indicated by a solid line for reference. The single-unit characteristics of the crystal unit 100 are obtained by taking out the crystal unit 100 alone and observing it from between the external electrodes 41 and 43.

In the single-unit characteristics of the crystal unit 100, in comparison with the same single-unit characteristics according to the sub-vibration illustrated in FIG. 5, the sub-vibration (e.g., frequency f2) has a smaller response than the main vibration (e.g., frequency f1). Although the frequency characteristics of impedance obtained from the terminals 202 and 204 (or the terminals 226 and 228) may be obtained under the state where the crystal unit 100 is mounted, it is not possible to observe a definite response that may be observed with the single-unit characteristics, as illustrated in FIG. 6. This is because the impedance between the terminals 202 and 204 (or the terminals 226 and 228) of the crystal unit includes not only the capacitance of the crystal unit 100 but also the capacitance of the matching capacitor 300, the IC internal capacitance (not illustrated), and the substrate stray capacitance (not illustrated).

In this respect, the external monitor terminals 110 and 112 (and the external electrodes 42 and 44) according to the sub-vibration are not electrically connected to the main vibration oscillation circuit 500 (see, e.g., FIG. 4). Accordingly, the impedance between the external monitor terminals 110 and 112 corresponds to the sum of the single-unit characteristics of the crystal unit 100 and some substrate stray capacitance. Accordingly, the impedance characteristics close to the single-unit characteristics of the crystal unit 100 may be obtained from the external monitor terminals 110 and 112. However, in the frequency characteristics of impedance obtained from the external monitor terminals 110 and 112 (see, e.g., the broken line in FIG. 5), it is difficult to observe a response according to the main vibration as compared to the single-unit characteristics of the crystal unit 100 (see, e.g., the solid line in FIG. 5). This is attributed to a relatively small response of the main vibration in the single-unit characteristics of the crystal unit 100 (see, e.g., the solid line in FIG. 5), the substrate stray capacitance and the like. In the meantime, as may be seen from FIG. 5, a response of the sub-vibration may be still observed.

In this way, according to this embodiment, as the frequency characteristics of impedance between the external electrodes 42 and 44 according to the sub-vibration, the impedance characteristics close to the single-unit characteristics of the crystal unit 100 may be obtained from the external monitor terminals 110 and 112 under the state where the crystal unit 100 is mounted. This allows the crystal unit 100 to be inspected under the state where the crystal unit 100 is mounted.

Figure 7:
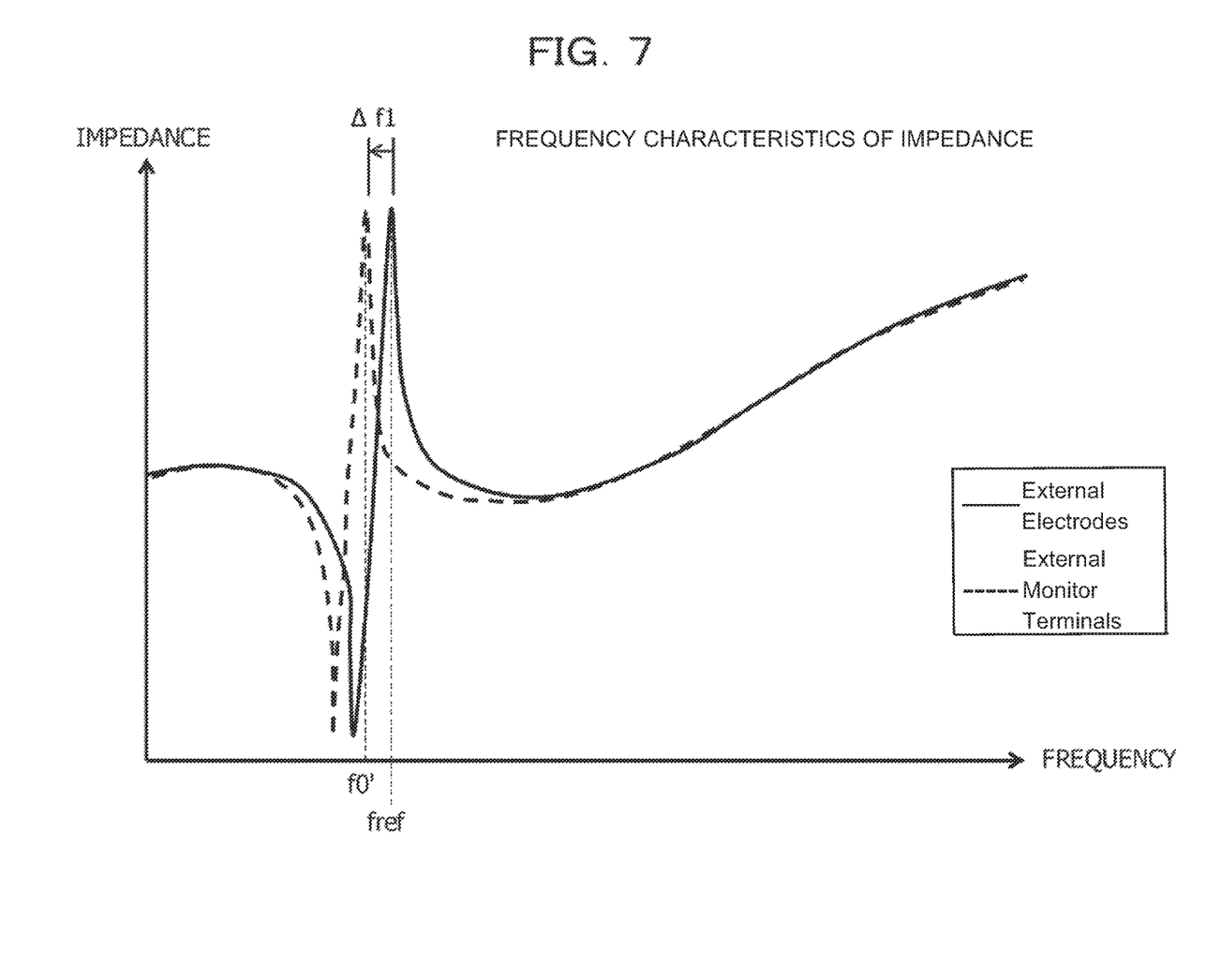
FIG. 7 is a view illustrating one example of the frequency characteristics of impedance between external electrodes 42 and 44 under the presence of defects.

FIG. 7 is a view illustrating one example of the frequency characteristics of impedance between the external electrodes 42 and 44 under the presence of defects. In FIG. 7, one example of the frequency characteristics when the crystal unit 100 is deteriorated with time is indicated by a dotted line and the same characteristics of the crystal unit 100 in a non-deteriorated state is indicated by a solid line. The frequency characteristics of impedance illustrated in FIG. 7 may be obtained from the external monitor terminals 110 and 112.

If the crystal unit 100 is deteriorated with time, the peak frequency according to the sub-vibration tends to be lower than the same peak frequency in the non-deteriorated state, as illustrated in FIG. 7. In the example illustrated in FIG. 7, the peak frequency according to the sub-vibration is decreased by $\Delta f1$ due to the deterioration with time. However, if the crystal unit 100 is deteriorated with time, the response according to the sub-vibration (e.g., peak value) tends not to be substantially changed as compared to the same response in the non-deteriorated state, as illustrated in FIG. 7. Accordingly, it is possible to determine the presence or absence of the time deterioration of the crystal unit 100 by determining the presence or absence of this tendency based the frequency characteristics of impedance between the external electrodes 42 and 44 obtained from the external monitor terminals 110 and 112 in the inspection.

For example, assuming that the peak frequency according to the sub-vibration in the non-deteriorated state is a reference frequency fref, the peak frequency according to the sub-vibration obtained under inspection (hereinafter referred to as "under-inspection peak frequency f0'") is compared with the reference frequency fref. Based on this comparison, it is possible to determine the time deterioration of the crystal unit 100. In this case, the reference frequency fref may be determined based on the peak frequency of a different individual (e.g., an average of peak frequencies for more different individuals) in the non-deteriorated state or may be determined based on the peak frequency of the same individual in the non-deteriorated state. For example, if the under-inspection peak frequency f0' is lower than the reference frequency fref by a first predetermined threshold or higher, the inspector may determine that the crystal unit 100 is defective.

The first predetermined threshold may be adapted by a test or the like. At this time, the inspector may compare the response according to the sub-vibration obtained under inspection (hereinafter referred to as "under-inspection response I0'") with a reference value Iref. Similarly, the reference value Iref may be determined based on the response of a different individual (e.g., an average of responses for more different individuals) in the non-deteriorated state or may be determined based on the response of the same individual in the non-deteriorated state. For example, if the under-inspection peak frequency f0' is lower than the reference frequency fref by the first predetermined threshold or higher and the under-inspection response I0' is not lower than the reference value Iref by a second predetermined threshold or higher, it may be determined that the crystal unit 100 is deteriorated with time. The second predetermined threshold is used to detect defects attributed to adhesion of alien substances as described later and may be adapted by a test or the like.

The determination on the presence or absence, or form of the above-mentioned defects (e.g., time deterioration) may be achieved by visual inspection of the inspector (e.g., comparison between data) or automatically achieved (e.g., by a program installed in a processor). This is equally applied to different forms of defects as described later.

Figure 8:
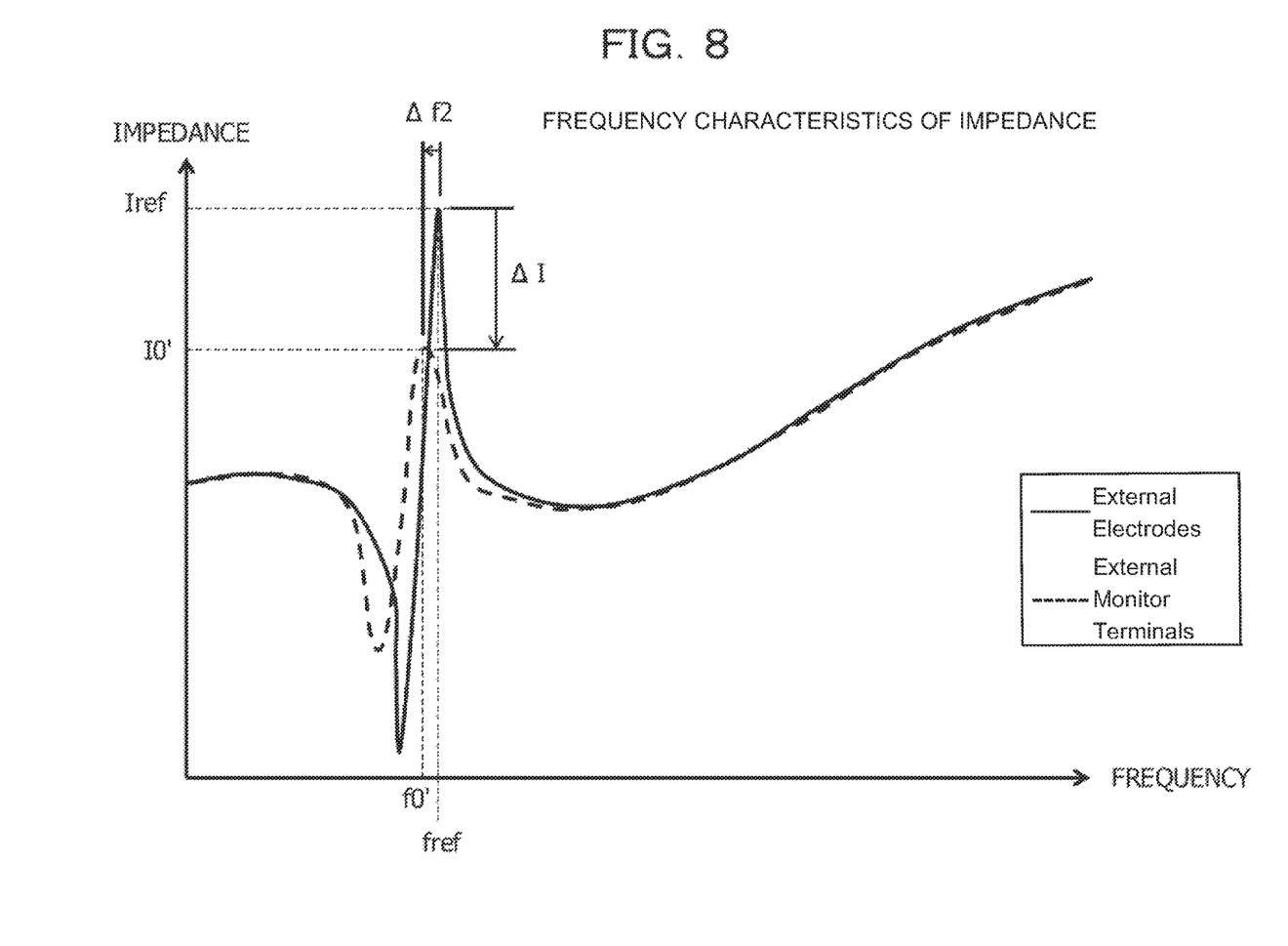
FIG. 8 is a view illustrating another example of the frequency characteristics of impedance between the external electrodes 42 and 44 under the presence of defects.

FIG. 8 is a view illustrating another example of the frequency characteristics of impedance between the external electrodes 42 and 44 under the presence of defects. In FIG. 8, one example of the frequency characteristics when alien substances are adhered to the crystal blank 10 of the crystal unit 100 is indicated by a dotted line and the same characteristics of the crystal unit 100 in the non-deteriorated state are indicated by a solid line. The frequency characteristics of impedance illustrated in FIG. 8 may be obtained from the external monitor terminals 110 and 112.

If alien substances are adhered to the crystal blank 10, the peak frequency according to the sub-vibration tends to be lower than the same peak frequency in the non-deteriorated state, as illustrated in FIG. 8. In the example illustrated in FIG. 8, the peak frequency according to the sub-vibration is decreased by $\Delta f2$ due to the adhesion of alien substances. In addition, if the alien substances are adhered to the crystal blank 10, the response according to the sub-vibration (e.g., a peak value) tends to be lower than the same response in the non-deteriorated state, as illustrated in FIG. 8. In the example illustrated in FIG. 8, the response according to the sub-vibration is decreased by $\Delta I$ due to the adhesion of alien substances. Accordingly, it is possible to determine the presence or absence of alien substances adhered to the crystal blank 10 by determining the presence or absence of this tendency based the frequency characteristics of impedance between the external electrodes 42 and 44 obtained from the external monitor terminals 110 and 112 in the inspection.

For example, the determination on the presence or absence of alien substances adhered to the crystal blank 10 may be made by comparing the reference frequency fref with the under-inspection peak frequency f0' and comparing the under-inspection response I0' with the reference value Iref. For example, if the under-inspection peak frequency f0' is lower than the reference frequency fref by a third predetermined threshold or higher and the under-inspection response I0' is lower than the reference value Iref by the second predetermined threshold or higher, the inspector may determine that alien substances are adhered to the crystal blank 10. The third predetermined threshold may be adapted by a test or the like.

Figure 9:
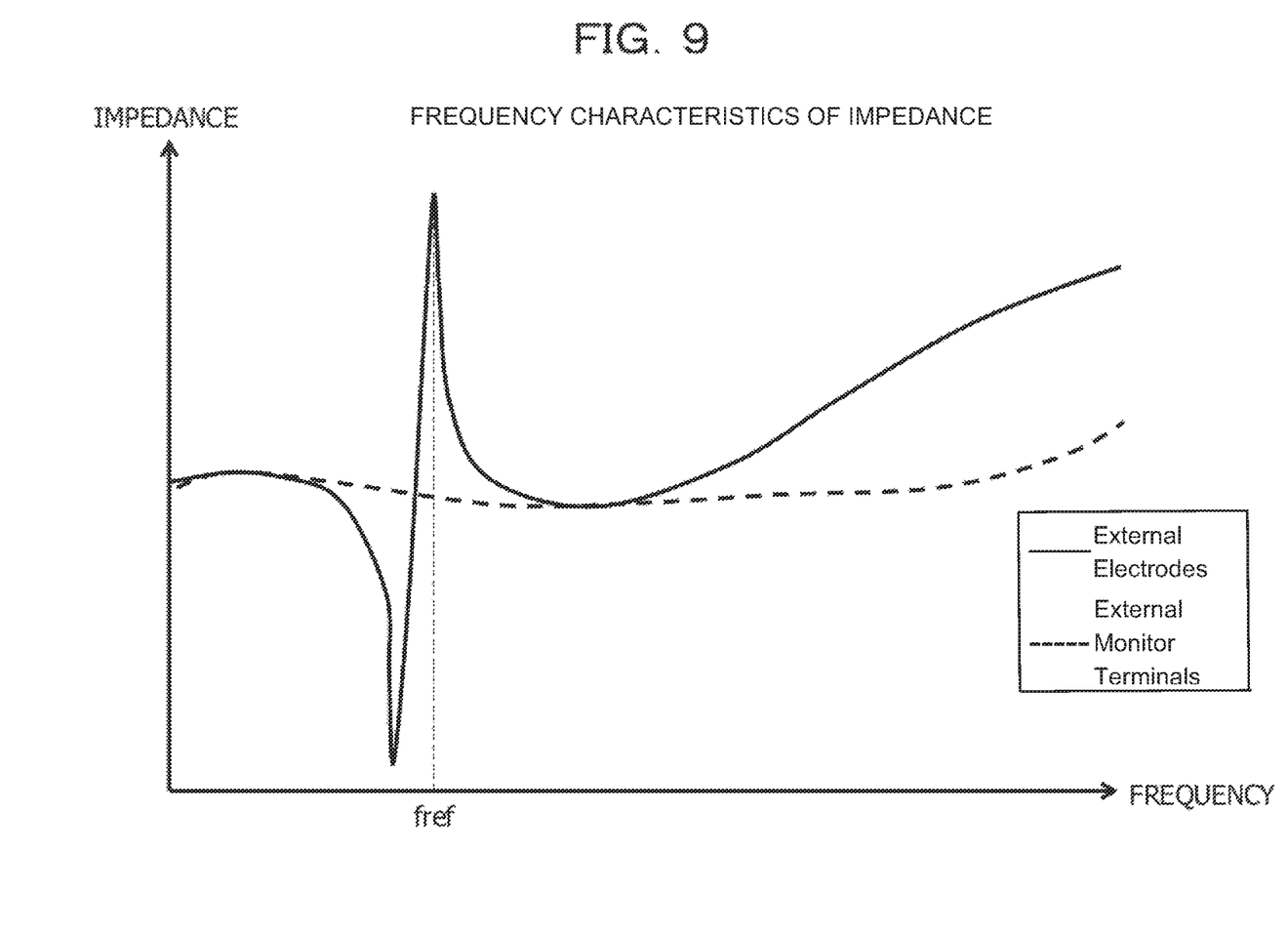
FIG. 9 is a view illustrating another example of the frequency characteristics of impedance between the external electrodes 42 and 44 under the presence of defects.

FIG. 9 is a view illustrating another example of the frequency characteristics of impedance between the external electrodes 42 and 44 under the presence of defects. In FIG. 9, one example of the frequency characteristics when the crystal blank 10 of the crystal unit 100 is damaged is indicated by a dotted line and the same characteristics of the crystal unit 100 in the non-deteriorated state are indicated by a solid line. The frequency characteristics of impedance illustrated in FIG. 9 may be obtained from the external monitor terminals 110 and 112.

If the crystal blank 10 is damaged, the impedance tends to be low over the entire frequency range, as illustrated in FIG. 9. Accordingly, it is possible to determine the presence or absence of damage of the crystal blank 10 by determining the presence or absence of this tendency based the frequency characteristics of impedance between the external electrodes 42 and 44 obtained from the external monitor terminals 110 and 112 in the inspection.

For example, the determination on the presence or absence of damage of the crystal blank 10 may be made based on the presence or absence of the under-inspection peak frequency f0' and the under-inspection response I0'. Specifically, if the under-inspection peak frequency f0' and the under-inspection response I0' may not be specified, the inspector may determine that the crystal blank 10 is damaged. Alternatively or equivalently, if the impedance obtained in the inspection is equal to or lower than a fourth predetermined threshold over the entire frequency range, the inspector may determine that the crystal blank 10 is damaged. The fourth predetermined threshold may be adapted by a test or the like.

In this way, according to this embodiment, based on the frequency characteristics of impedance between the external electrodes 42 and 44 obtained from the external monitor terminals 110 and 112 in the inspection, it is possible to determine the presence or absence of time deterioration of the crystal unit 100, the presence or absence of alien substances adhered to the crystal unit 100, and the presence or absence of damage.

In addition, although the determination on the presence or absence, or form of the above-mentioned defects (e.g., time deterioration and so on) is made based on the determination on whether or not values (e.g., f0' and I0') in the inspection are deviated from the corresponding reference values (fref and Iref) by the corresponding predetermined thresholds or higher, the present disclosure is not limited thereto.

For example, equivalently, the determination on the presence or absence, or form of the above-mentioned defects (e.g., time deterioration and so on) may be made based on the determination on whether or not the values (e.g., f0' and I0') in the inspection fall within the corresponding reference ranges. Alternatively, the determination on the presence or absence, or form of the above-mentioned defects (e.g., time deterioration and so on) may be made by comparing the frequency characteristics of impedance between the external electrodes 42 and 44 obtained from the external monitor terminals 110 and 112 in the inspection with the frequency characteristics of impedance serving as a reference. The frequency characteristics of impedance serving as a reference may be the frequency characteristics of different individuals in the non-deteriorated state or the frequency characteristics of the same individuals in the non-deteriorated state.

In recent years, in an effort to meet the requirements of reduction in device size, compactness and high-density packaging of parts and modules are in progress. With no exception, the downsizing of the crystal units serving as clock sources have also been in progress with the sizes of, for example, 3.2×2.5 mm, 2.5×2.0 mm and 2.0×1.6 mm. Under such circumstances, when it is considered that a function failure has occurred in a device due to an abnormality of a crystal unit, it is useful to provide the ability to inspect the crystal unit in a state where it is packaged into the device. This is because taking out and inspecting only the crystal unit 100 in a high-density packaging involves a risk of damaging peripheral parts when the crystal unit 100 is removed from the device.

Figure 10:
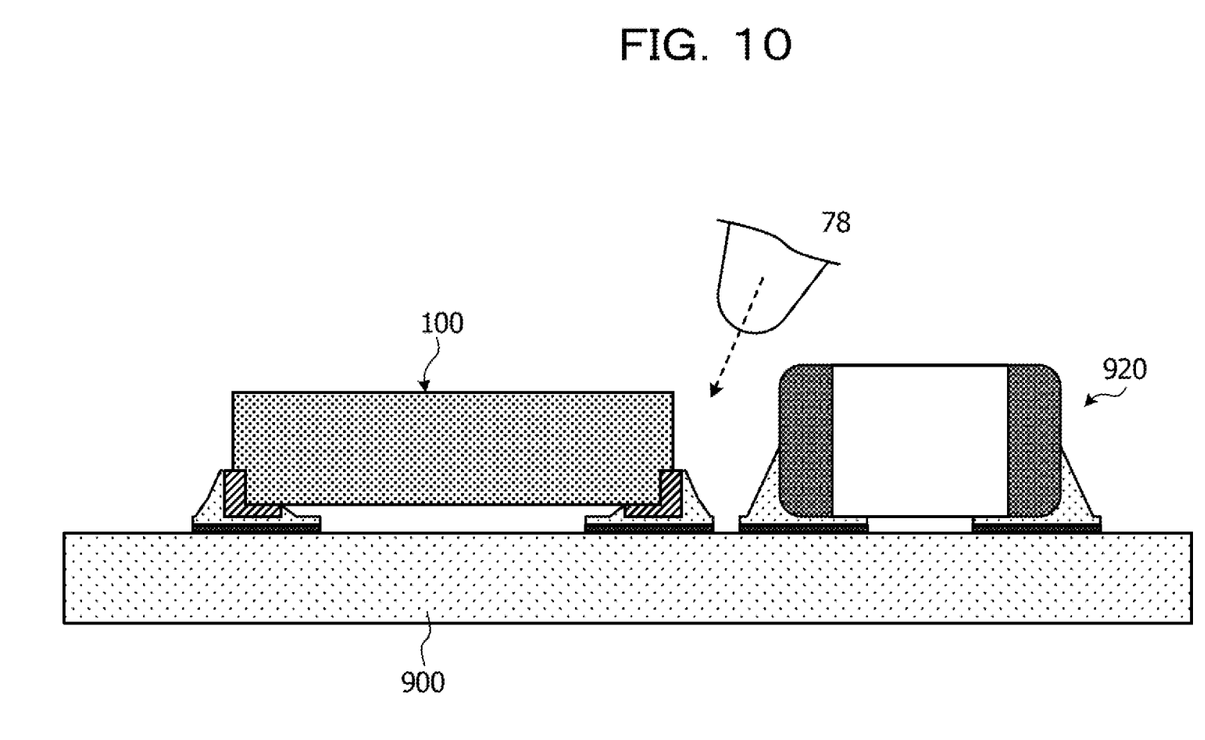
FIG. 10 is a view illustrating one example of a state where the crystal unit 100 is mounted.

In this respect, probe inspection of high impedance may be possible in the state where the crystal unit 100 is mounted. However, with recent compactness, in some cases, terminals (see, e.g., the terminals 220 and 222 in FIG. 3) through which an oscillation state may be identified may not be contained in the IC 200 or may be hidden in the back side of the IC package by Ball Grid Array (BGA). In addition, in some cases, there may be states where no probing point is present, such as incorporating the matching capacitor 300 in the IC 200, forming terminals in the back side of the crystal unit 100, etc. In addition, in some cases, with advance of high-density packaging, there may be no place to which a probe 78 is to be physically applied, as schematically illustrated in FIG. 10. In the example illustrated in FIG. 10, the crystal unit 100 is mounted on a board (e.g., a mother board) 900, together with ambient peripheral parts 920.

In this respect, according to the inspection method of this embodiment, as described above, even if the probe inspection using the terminals 220 and 222 and so on is impossible or difficult, it is possible to inspect the crystal unit 100 with high precision. In addition, according to the inspection method of this embodiment, it is possible to inspect a state of the single crystal blank 10 with higher precision than an inspection method based on an output from the terminals 220 and 222. This is because characteristics of elements (e.g., the IC 200, the matching capacitor 300 and the like) other than the crystal blank 10 are superimposed on the output from the terminals 220 and 222 (see, e.g., the broken line in FIG. 6) whereas such characteristics are not superimposed on the output from the external monitor terminals 110 and 112.

Next, another inspection method which does not use the analyzer 350 will be described with reference to FIG. 11.

Figure 11:
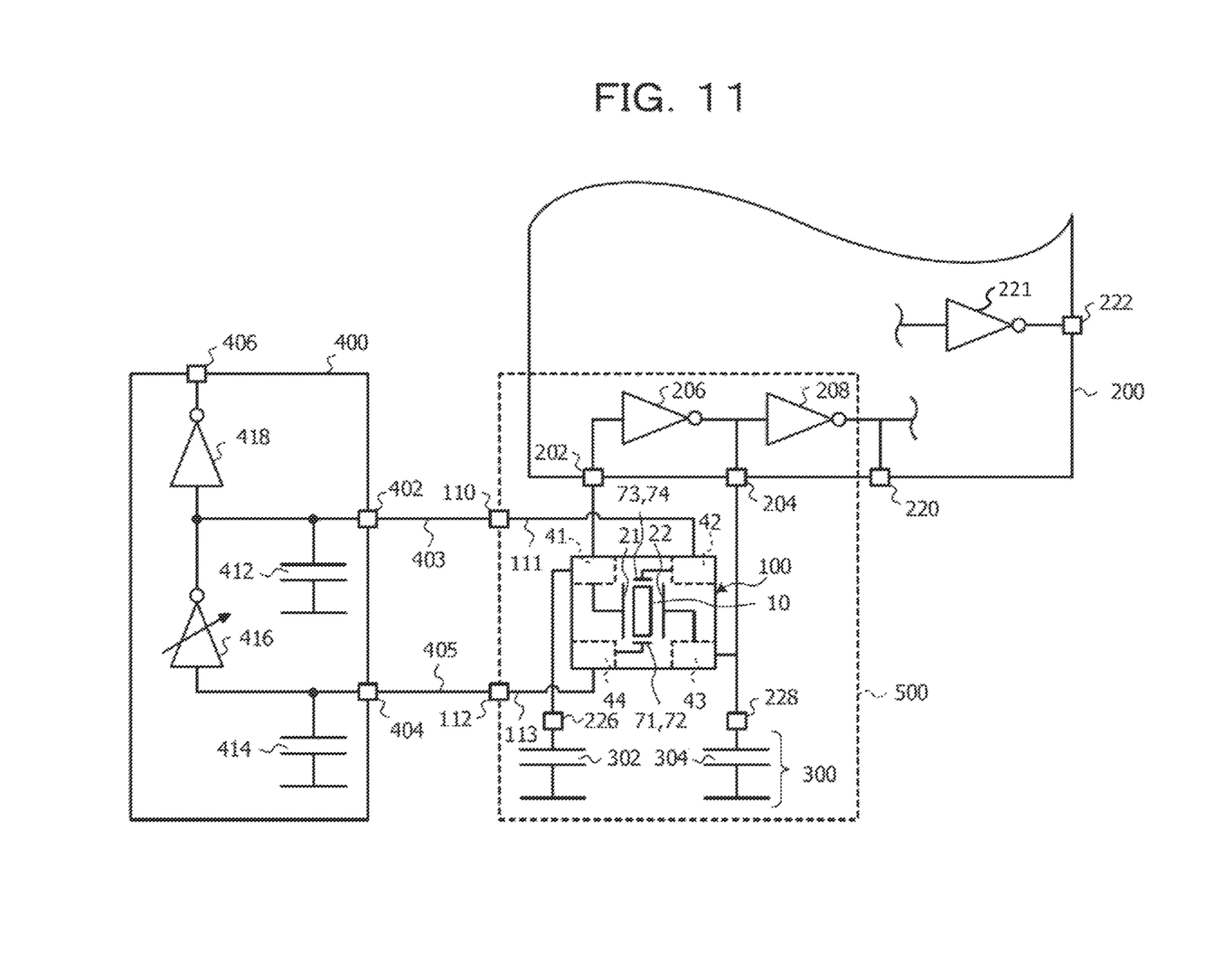
FIG. 11 is an explanatory view of another method of inspecting the crystal unit 100.

FIG. 11 is an explanatory view of another method of inspecting the crystal unit 100, schematically illustrating a state of the crystal unit 100 in inspection.

Another method of inspecting the crystal unit 100 as described below may be performed under the state where the crystal unit 100 is mounted. Specifically, as schematically illustrated in FIG. 11, a sub-vibration oscillation circuit 400 is connected to the mounted crystal unit 100 via wirings 403 and 405. The wirings 403 and 405 to external terminals 402 and 404 of the sub-vibration oscillation circuit 400 is formed, for example by applying a probe (not illustrated) to the external monitor terminals 110 and 112. In addition, like the inspection method described with reference to FIG. 4, if the probe may be directly easily applied to the external electrodes 42 and 44 under the state where the crystal unit 100 is mounted, the wirings 111 and 113 and the external monitor terminals 110 and 112 may be omitted. In this case, an inspector may make an electrical connection of the sub-vibration oscillation circuit 400 to the external electrodes 42 and 44 by directly applying the probe to the external electrodes 42 and 44 under the state where the crystal unit 100 is mounted.

The sub-vibration oscillation circuit 400 includes substantially the same elements as the main vibration oscillation circuit 500. Specifically, the sub-vibration oscillation circuit 400 includes matching capacitors 412 and 414, an inverting amplifier 416 and an output buffer 418. The inverting amplifier 416 may be a variable gain amplifier as illustrated in FIG. 11. The sub-vibration oscillation circuit 400 further includes external terminals 402, 404 and 406.

An inspector applies an input signal (noise) to the sub-vibration electrode 70 via the wiring 403 by powering on the inverting amplifier 416 of the sub-vibration oscillation circuit 400 under a state where the main vibration of the crystal unit 100 is stopped. As a result, the sub-vibration of the crystal unit 100 is excited. The inspector may obtain an output for the input signal, which is applied to the crystal unit 100, via an external terminal 406.

An output waveform (e.g., a pulse waveform) according to the sub-vibration of the crystal unit 100 is output from the external terminal 406. The frequency of the output waveform is a frequency according to the sub-vibration and corresponds to the above-described under-inspection peak frequency f0'. Accordingly, the inspector may determine the presence or absence of defects of the crystal unit 100, like the inspection method described with reference to FIG. 4, by comparing the frequency of the output waveform with the reference frequency fref. In addition, the frequency of the output waveform from the external terminal 406 may be specified, for example by a frequency counter. In this way, the inspector may inspect the crystal unit 100 by connecting the sub-vibration oscillation circuit 400 to the external monitor terminals 110 and 112 and exciting the sub-vibration of the crystal unit 100.

In addition, in the inspection method illustrated in FIG. 11, the inspector may create an over-excited state by increasing the gain of the inverting amplifier 416 and make a change in a vibration state (e.g., such as normal oscillation). This may be effective particularly when the form of defects is adhesion of alien substances since the alien substances may be removed by the over-excitation.

While various embodiments have been described in the above, the disclosed embodiments are not intended to have a limited sense but may be modified and altered in various ways without departing from the spirit and scope of the invention defined in the claims. In addition, combinations of all or some of elements described in the above embodiments may be made.

For example, although it has been illustrated in the above embodiments that the sub-vibration is the specific form of contour vibration (e.g., a form having a node near the center of each side) as illustrated in FIG. 2, the sub-vibration may be different forms of contour vibrations.

In addition, although it has been illustrated in the above embodiments that the outer shape of the crystal blank 10 is rectangular, the crystal blank 10 may have different outer shapes.

In addition, although it has been illustrated in the above embodiments that the inspection is performed under the state where the main vibration of the crystal unit 100 is stopped, the inspection may be performed under a state where the main vibration of the crystal unit 100 is generated. This is because the wirings 111 and 113 and the external monitor terminals 110 and 112 are electrically isolated from the main vibration oscillation circuit 500, as described above.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to an illustrating of the superiority and inferiority of the invention. Although the embodiments of the present invention have been described in detail, it should be understood that the various changes, substitutions, and alterations could be made hereto without departing from the spirit and scope of the invention.

What is claimed is:

1. A method of inspecting comprising:
    providing a crystal oscillator including a crystal blank, a main-vibration electrode, and a housing that houses the crystal blank and the main-vibration electrode;
    providing a plurality of sub-vibration electrodes on the crystal blank along with the main-vibration electrode of the crystal oscillator including an oscillation circuit;
    generating a sub-vibration in the crystal blank of the crystal oscillator by generating an alternating electric field between the plurality of sub-vibration electrodes formed on the crystal blank using an analyzer while a main-vibration by the main-vibration electrode is stopped and the crystal oscillator is in a built-in state with a packaged device that includes a circuit having a different function from the oscillation circuit and uses a clock signal generated from the crystal oscillator;
    obtaining frequency characteristics of impedance between the plurality of sub-vibration electrodes using the analyzer from an output signal of the plurality of sub-vibration electrodes by scanning frequency of the input signal from the analyzer;
    comparing the frequency characteristics of impedance obtained at the obtaining with reference frequency characteristics of impedance prepared in advance indicating quality of the crystal oscillator when the crystal oscillator is in a normal condition; and
    determining whether the crystal oscillator is in the normal condition or in an abnormal condition based on a result from the comparing while the crystal oscillator is in the built-in state with the packaged device, wherein the generating the sub-vibration applies a first sinusoidal wave to a portion of the plurality of sub-vibration electrodes and applies a second sinusoidal wave having an opposite phase to the first sinusoidal wave to the rest of the plurality of sub-vibration electrodes in order to generate the alternating electric field between the plurality of sub-vibration electrodes and causes a change in contour of the crystal blank by the alternating electric field.

2. The method according to claim 1, wherein the main-vibration electrode is electrically separated from the plurality of sub-vibration electrodes.

3. The method according to claim 1 further comprising: specifying at least one of a peak value of an impedance and a peak frequency where the impedance is in the peak value from the frequency characteristics of impedance obtained at the obtaining according to the sub-vibration.

4. The method according to claim 3 further comprising: comparing at least one of the peak frequency and the peak value in the frequency characteristics of impedance obtained at the specifying according to the sub-vibration with a corresponding reference value or reference range in the reference frequency characteristics of impedance prepared in advance.

5. The method according to claim 3 further comprising:
comparing each of the peak frequency and the peak value in the frequency characteristics of impedance with each corresponding reference value or reference range in the reference frequency characteristics of impedance prepared in advance; and determining a form of defect of the crystal oscillator as the abnormal condition of the crystal oscillator based on the result of the comparing each of the peak frequency and the peak value in the frequency characteristics of impedance with each corresponding reference value or reference range in the reference frequency characteristics of impedance prepared in advance.

6. The method according to claim 5, wherein the form of defect is one of a time deterioration of the crystal oscillator, an adhesion of alien substance to the crystal oscillator, and a damage to the crystal oscillator.

* * * * *